(12) United States Patent
Dolling et al.

(10) Patent No.: US 6,172,235 B1
(45) Date of Patent: Jan. 9, 2001

(54) ASYMMETRIC CONJUGATE ADDITION REACTION

(75) Inventors: Ulf H. Dolling, Westfield; Lisa F. Frey, Somerset; Richard D. Tillyer, Cranford; David M. Tschaen, Holmdel, all of NJ (US)

(73) Assignee: Merck & Co., Inc., Rahway, NJ (US)

( * ) Notice: Under 35 U.S.C. 154(b), the term of this patent shall be extended for 0 days.

(21) Appl. No.: 09/242,143

(22) PCT Filed: Aug. 5, 1997

(86) PCT No.: PCT/US97/13725

§ 371 Date: Apr. 27, 1999

§ 102(e) Date: Apr. 27, 1999

(87) PCT Pub. No.: WO98/06698

PCT Pub. Date: Feb. 19, 1998

Related U.S. Application Data

(60) Provisional application No. 60/023,619, filed on Aug. 9, 1996, and provisional application No. 60/028,233, filed on Oct. 10, 1996.

(51) Int. Cl.⁷ .................................................. C07D 213/02
(52) U.S. Cl. ........................................ 546/283.7; 546/343
(58) Field of Search ................................. 546/343, 283.7

(56) References Cited

U.S. PATENT DOCUMENTS

| 5,017,608 | 5/1991 | Ashwanden et al. ................... 514/80 |
| 5,389,620 | 2/1995 | Ishikawa et al. ..................... 514/538 |

FOREIGN PATENT DOCUMENTS

| WO 93/08799 | 5/1993 | (WO) . |
| WO 98/06700 | 2/1998 | (WO) . |

OTHER PUBLICATIONS

Alexakis, et al., Tetrahedron Letters, vol. 29(35), pp. 4411–4414, 1988.

Shinohara, et al., Bull. Chem. Soc., Japan, vol. 38, pp. 1, 3, 1965.

Alexakis, A., et al., Tetrahedron Lett., vol. 31(3), pp. 345–348, 1990.

Frey, L.F., et al., J. Org. Chem., vol. 63(9), pp. 3120–3124, 1998.

*Primary Examiner*—Zinna Northington Davis
(74) *Attorney, Agent, or Firm*—Valerie J. Camara; Mark R. Daniel

(57) ABSTRACT

This invention relates to a key intermediate in the synthesis of an endothelin antagonist and the synthesis of this key intermediate using an asymmetric conjugate addition reaction.

31 Claims, No Drawings

ASYMMETRIC CONJUGATE ADDITION REACTION

This application is a 371 application of PCT/US97/13725 filed Aug. 5, 1997 which claims the benefit of priority to Provisional Application Ser. No. 60/023,619 filed Aug. 9, 1996 and Provisional Application Ser. No. 60/028,233 filed Oct. 10, 1996.

BACKGROUND OF THE INVENTION

The present invention relates to novel key intermediates in the synthesis of an endothelin antagonist and the method for preparing these key intermediates of formula 1.

Two endothelin receptor subtypes $ET_A$ and $ET_B$ are known so far. The compounds of the present invention possess high affinity to at least one of two receptor subtypes, responsible for the dilation of smooth muscle, such as blood vessels or in the trachea. The endothelin antagonist compounds of the present invention provide a new therapeutic potential, particularly for the treatment of hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, restenosis, prostatauxe endotoxin shock, endotoxin-induced multiple organ failure or disseminated intravascular coagulation, and/or cyclosporin-induced renal failure or hypertension.

Endothelin is a polypeptide composed of amino acids, and it is produced by vascular endothelial cells of human or pig. Endothelin has a potent vasoconstrictor effect and a sustained and potent pressor action (Nature, 332, 41 1–415 (1988)).

Three endothelin isopeptides (endothelin-1, endothelin-2 and endothelin-3), which resemble one another in structure, exist in the bodies of animals including human, and these peptides have vasoconstriction and pressor effects (Proc. Natl. Acad, Sci, USA, 86, 2863–2867 (1989)).

As reported, the endothelin levels are clearly elevated in the blood of patients with essential hypertension, acute myocardial infarction, pulmonary hypertension, Raynaud's disease, diabetes or atherosclerosis, or in the washing fluids of the respiratory tract or the blood of patients with asthmaticus as compared with normal levels (Japan, J. Hypertension, 12, 79, (1989), J. Vascular medicine Biology, 2, 207 (1990), Diabetologia, 33, 306–310 (1990), J. Am. Med. Association, 264, 2868 (1990), and The Lancet, ii, 747–748 (1989) and ii, 1144–1147 (1990)).

Further, an increased sensitivity of the cerebral blood vessel to endothelin in an experimental model of cerebral vasospasm (Japan. Soc. Cereb. Blood Flow & Metabol., 1, 73 (1989)), an improved renal function by the endothelin antibody in an acute renal failure model (J. Clin, invest., 83, 1762–1767 (1989), and inhibition of gastric ulcer development with an endothelin antibody in a gastric ulcer model (Extract of Japanese Society of Experimental Gastric Ulcer, 50 (1991)) have been reported. Therefore, endothelin is assumed to be one of the mediators causing acute renal failure or cerebral vasospasm following subarachnoid hemorrhage.

Further, endothelin is secreted not only by endothelial cells but also by tracheal epithelial cells or by kidney cells (FEBS Letters, 255, 129–132 (1989), and FEBS Letters, 249, 42–46 (1989)).

Endothelin was also found to control the release of physiologically active endogenous substances such as renin, atrial natriuretic peptide, endothelium-derived relaxing factor (EDRF), thromboxane $A_2$, prostacyclin, noradrenaline, angiotensin II and substance P (Biochem. Biophys, Res. Commun., 157, 1164–1168 (1988); Biochem. Biophys, Res. Commun., 155, 20 167–172 (1989); Proc. Natl. Acad. Sci. USA, 85 1 9797–9800 (1989); J. Cardiovasc. Pharmacol., 13, S89–S92 (1989); Japan. J. Hypertension, 12, 76 (1989) and Neuroscience Letters, 102, 179–184 (1989)). Further, endothelin causes contraction of the smooth muscle of gastrointestinal tract and the uterine smooth muscle (FEBS Letters, 247, 337–340 (1989); Eur. J. Pharmacol., 154, 227–228 (1988); and Biochem. Biophys Res. Commun., 159, 317–323 (1989)). Further, endothelin was found to promote proliferation of rat vascular smooth muscle cells, suggesting a possible relevance to the arterial hypertrophy (Atherosclerosis, 78, 225–228 (1989)). Furthermore, since the endothelin receptors are present in a high density not only in the peripheral tissues but also in the central nervous system, and the cerebral administration of endothelin induces a behavioral change in animals, endothelin is likely to play an important role for controlling nervous functions (Neuroscience Letters, 97, 276–279 (1989)). Particularly, endothelin is suggested to be one of mediators for pain (Life Sciences, 49, PL61–PL65 (1991)).

Internal hyperplastic response was induced by rat carotid artery balloon endothelial denudation. Endothelin causes a significant worsening of the internal hyperplasia (J. Cardiovasc. Pharmacol., 22, 355–359 & 371–373(1993)). These data support a role of endothelin in the pathogenesis of vascular restenosis. Recently, it has been reported that both $ET_A$ and $ET_B$ receptors exist in the human prostate and endothelin produces a potent contraction of it. These results suggest the possibility that endothelin is involved in the pathophysiology of benign prostatic hyperplasia (J. Urology, 151, 763–766(1994), Molecular Pharmacol., 45, 306–311 (1994)).

On the other hand, endotoxin is one of potential candidates to promote the release of endothelin. Remarkable elevation of the endothelin levels in the blood or in the culture supernatant of endothelial cells was observed when endotoxin was exogenously administered to animals or added to the culture endothelial cells, respectively. These findings suggest that endothelin is an important mediator for endotoxin-induced diseases (Biochem. Biophys. Commun., 161, 1220–1227 (1989); and Acta Physiol. Scand., 137, 317–318 (1989)).

Further, it was reported that cyclosporin remarkably increased endothelin secretion in the renal cell culture (LLC-PKL cells) (Eur. J. Pharmacol., 180, 191–192 (1990)). Further, dosing of cyclosporin to rats reduced the glomerular filtration rate and increased the blood pressure in association with a remarkable increase in the circulating endothelin level. This cyclosporin-inducea renal failure can be suppressed by the administration of endothelin antibody (Kidney Int., 37, 1487–1491 (1990)). Thus, it is assumed that endothelin is significantly involved in the pathogenesis of the cyclosporin-induced diseases.

Such various effects of endothelin are caused by the binding of endothelin to endothelin receptors widely distributed in many tissues (Am. J. Physiol., 256, R856–R866 (1989)).

It is known that vasoconstriction by the endothelins is caused via at least two subtypes of endothelin receptors (J. Cardiovasc. Pharmacol., 17(Suppl.7), S119–S121 (1991)). One of the endothelin receptors is $ET_A$ receptor Selective to ET-1 rather than ET-3, and the other is $ET_B$ receptor equally active to ET-1 and ET-3. These receptor proteins are reported to be different from each other (Nature, 348, 730–735 (1990)).

These two subtypes of endothelin receptors are differently distributed in tissues. It is known that the $ET_A$ receptor is present mainly in cardiovascular tissues, whereas the $ET_B$ receptor is widely distributed in various tissues such as brain, kidney, lung, heart and vascular tissues.

Substances which specifically inhibit the binding of endothelin to the endothelin receptors are believed to antagonize various pharmacological activities of endothelin and to be useful as a drug in a wide field. Since the action of the endothelins is caused via not only the $ET_A$ receptor but also the $ET_B$ receptor, novel non-peptidic substances with ET receptor antagonistic activity to either receptor subtype are desired to block activities of the endothelins effectively in various diseases.

Endothelin is an endogenous substance which directly or indirectly (by controlling liberation of various endogenous substances) induces sustained contraction or relaxation of vascular or non-vascular smooth muscles, and its excess production or excess secretion is believed to be one of pathogeneses for hypertension, pulmonary hypertension, Raynaud's disease, bronchial asthma, gastric ulcer, diabetes, arteriosclerosis, restenosis, acute renal failure, myocardial infarction, angina pectoris, cerebral vasospasm and cerebral infarction. Further, it is suggested that endothelin serves as an important mediator involved in diseases such as restenosis, prostatauxe, endotoxin shock, endotoxin-induced multiple organ failure or disseminated intravascular coagulation, and cyclosporin-induced renal failure or hypertension. Two endothelin receptors $ET_A$ and $ET_B$ are known so far. An antagonistic agent against the $ET_B$ receptor as well as the $ET_A$ receptor is useful as a drug. In the field of anti-endothelin agents, some non-peptidic compounds possessing antagonistic activity against endothelin receptors were already disclosed in patents (for example, EP 0526708 Al, WO 93/08799 Al). Accordingly, it is an object of the present invention to provide a novel therapeutics for the treatment of the above-mentioned various diseases by an invention of a novel and potent non-peptidic antagonist against either $ET_A$ or $ET_B$ receptor.

In order to accomplish the above object, the present inventors have developed an asymmetric conjugate addition which enables them to prepare the compound of Formula I,

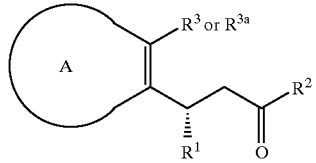

I a key intermediate in the synthesis of endothelin antagonists of the following structure:

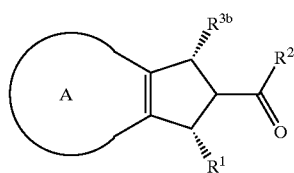

wherein

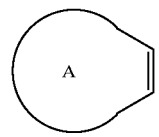

represents: 5- or 6-membered heterocyclyl, 5- or 6-membered carbocyclyl, and aryl;
$R^{3b}$ is aryl, or heteroaryl;
$R^1$ is: $C_1$–$C_8$ alkyl, $C_2$–$C_8$ alkenyl, $C_2$–$C_8$ alkynyl, $C_3$–$C_8$ cycloalkyl, aryl, or heteroaryl;
$R^2$ is $OR^4$ and $N(R^5)_2$;
$R^4$ is $C_1$–$C_8$ alkyl; and
$R^5$ is: $C_1$–$C_8$ alkyl, or aryl.

SUMMARY OF THE INVENTION

This invention relates to a key intermediate in the synthesis of an endothelin antagonist and the synthesis of this key intermediate using an asymmetric conjugate addition reaction.

The instant invention relates to a compound of formula I:

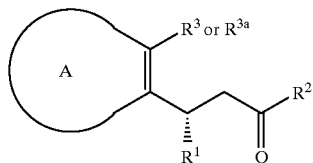

I wherein

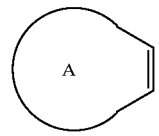

represents:
a) 5- or 6-membered heterocyclyl containing one, two or three double bonds, but at least one double bond and 1, 2 or 3 heteroatoms selected from O, N and S, the heterocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$,
b) 5- or 6-membered carbocyclyl containing one or two double bonds, but at least one double bond, the carbocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, c) aryl, wherein aryl is as defined below,
   $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, $CO(CH_2)_nCH_3$, and $CO(CH_2)_nCH_2N(R^5)_2$,
   aryl is defined as phenyl or naphthyl, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$, and when two substituents are located on adjacent carbons they can join to form a 5- or 6-membered ring with one, two or three heteroatoms selected from O, N, and S, which is unsubstituted or substituted with with one, two or three substituents selected from the group consisting of: H, OH, $CO_2R^6$, Br, Cl, F, I, $CF_3$, $N(R^7)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$,
   n is 0 to 5;

$R^1$ is:
a) $C_1$–$C_8$ alkyl, $C_2$–$C_8$ alkenyl, $C_2$–$C_8$ alkynyl, $C_3$–$C_8$ cycloalkyl,
b) aryl, or
c) heteroaryl;
   heteroaryl is defined as a 5- or 6-membered aromatic ring containing 1, 2 or 3 heteroatoms selected from O, N and S which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, $R^2$ is $OR^4$ or $N(R^5)_2$;

$R^3$ is 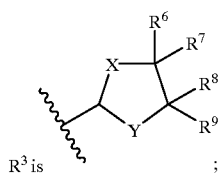

$R^{3a}$ is:
a) CHO,
b) —CO-$C_1$–$C_8$ alkyl,
c) —CO-aryl, or
d) —CO-heteroaryl;

X and Y are independently: O, S, or $NR^5$;
$R^4$ is $C_1$–$C_8$ alkyl;
$R^5$ is: $C_1$–$C_8$ alkyl, or aryl; and
$R^6$, $R^7$, $R^8$ and $R^9$ are independently: H, $C_1$–$C_8$ alkyl, and aryl, such that either $R^6$ and $R^7$ are not the same and/or $R^8$ and $R^9$ are not the same, or $R^6$ and $R^8$ or $R^7$ and $R^9$ can join to form a 5- or 6-membered ring, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$.

Also within the scope of the instant invention is a process for the preparation of a compound of formula I:

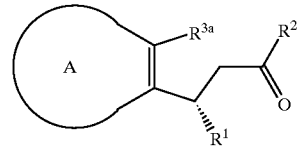

I wherein the substituents are as defined above, comprising reacting a α,β-unsaturated ester or amide

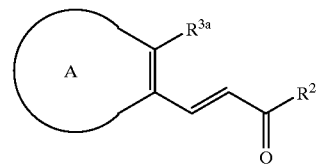

with an organolithium compound, $R^1Li$, in the presence of an aprotic solvent at a temperature range of about −79° C. to about 0° C.

Also within the scope of the instant invention is a process for the preparation of the compound of formula I:

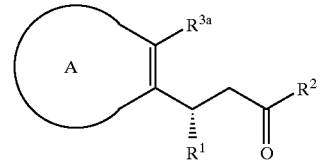

I wherein the substituents are as defined above, comprising the steps of:

1) reacting an α,β-unsaturated ester or amide

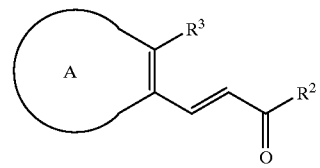

with an organolithium compound, $R^1Li$, in the presence of an aprotic solvent at a temperature range of about −78° C. to about 0° C. to give the conjugate adduct, and 2) removing the chiral auxiliary, $R^3$, with aqueous acid and tetrahydrofuran to give the compound of Formula I.

DETAILED DESCRIPTION OF THE INVENTION

The instant invention relates to a compound of formula I:

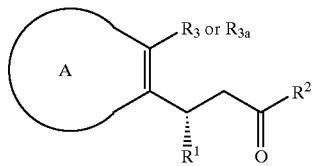

wherein

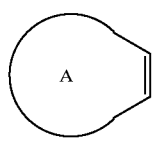

represents:
a) 5- or 6-membered heterocyclyl containing one, two or three double bonds, but at least one double bond and 1, 2 or 3 heteroatoms selected from O, N and S, the heterocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$,
b) 5- or 6-membered carbocyclyl containing one or two double bonds, but at least one double bond, the carbocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$,
c) aryl, wherein aryl is as defined below,
   $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, $CO(CH_2)_nCH_3$, and $CO(CH_2)_nCH_2N(R^5)_2$,
   aryl is defined as phenyl or naphthyl, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$, and when two substituents are located on adjacent carbons they can join to form a 5- or 6-membered ring with one, two or three heteroatoms selected from O, N, and S, which is unsubstituted or substituted with one, two or three substituents selected from the group consisting of: H, OH, $CO_2R^6$, Br, Cl, F, I, $CF_3$, $N(R^7)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$,
   n is 0 to 5;
$R^1$ is:
a) $C_1$–$C_8$ alkyl, $C_2$–$C_8$ alkenyl, $C_2$–$C_8$ alkynyl, $C_3$–$C_8$ cycloalkyl,
b) aryl, or
c) heteroaryl;
   heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$,
$R^2$ is $OR^4$ or $N(R^5)_2$;

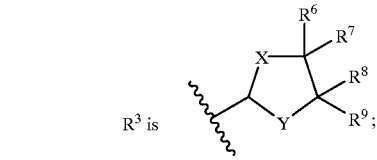

$R^{3a}$ is:
a) CHO,
b) —CO-$C_1$–$C_8$ alkyl,
c) —CO-aryl, or
d) —CO-heteroaryl;
X and Y are independently: O, S, or $NR^5$;
$R^4$ is $C_1$–$C_8$ alkyl;
$R^5$ is: $C_1$–$C_8$ alkyl, or aryl; and
$R^6$, $R^7$, $R^8$ and $R^9$ are independently: H, $C_1$–$C_8$ alkyl, and aryl, such that either $R^6$ and $R^7$ are not the same and/or $R^8$ and $R^9$ are not the same, or $R^6$ and $R^8$ or $R^7$ and $R^9$ can join to form a 5- or 6-membered ring, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$.

The instant invention also relates to a process for the preparation of a compound of formula I:

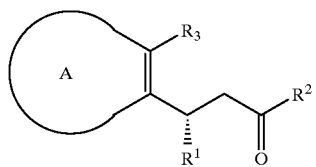

wherein

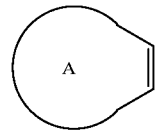

represents:
a) 5- or 6-membered heterocyclyl containing one, two or three double bonds, but at least one double bond and 1, 2 or 3 heteroatoms selected from O, N and S, the heterocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, b) 5- or 6-membered carbocyclyl containing one or two double bonds, but at least one double bond, the carbocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, c) aryl, wherein aryl is as defined below, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, $CO(CH_2)_nCH_3$, and $CO(CH_2)_nCH_2N(R^5)_2$, aryl is defined as phenyl or naphthyl, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$, and when two substituents are located on adjacent carbons they can join to form a 5- or 6-membered ling with one, two or three heteroatoms selected from O, N, and S, which is unsubstituted or substituted with one, two or three substituents selected from the group consisting of: H, OH, $CO_2R^6$, Br, Cl, F, I, $CF_3$, $N(R^7)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, n is 0 to 5;

$R^1$ is:

a) $C_1$–$C_8$ alkyl, $C_2$–$C_8$ alkenyl, $C_2$–$C_8$ alkynyl, $C_3$–$C_8$ cycloalkyl, b) aryl, or c) heteroaryl;

heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, $R^2$ is $OR^4$ or $N(R^5)_2$;

$R^3$ is 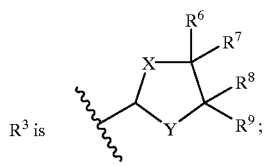

$R^{3a}$ is:

a) CHO, b) —CO-$C_1$–$C_8$ alkyl, c) —CO-aryl, or d) —CO-heteroaryl;

X and Y are independently: O, S, or $NR^5$;

$R^4$ is $C_1$–$C_8$ alkyl;

$R^5$ is: $C_1$–$C_8$ alkyl, or aryl; and $R^6$, $R^7$, $R^8$ and $R^9$ are independently: H, $C_1$–$C_8$ alkyl, and aryl, such that either $R^6$ and $R^7$ are not the same and/or $R^8$ and $R^9$ are not the same, or $R^6$ and $R_8$ or $R^7$ and $R^9$ can join to form a 5- or 6-membered ring, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$;

comprising reacting a α,β-unsaturated ester or amide

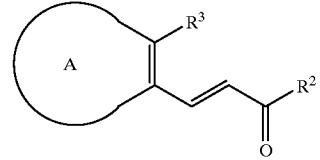

with an organolithium compound, $R^1Li$, in the presence of an aprotic solvent at a temperature range of about –78° C. to about 0° C.

The process as recited above, wherein the number of equivalents of the organolithium compound, $R^1Li$, is 1 to about 4. The process as recited above, wherein the aprotic solvent is selected from the group consisting of tetrahydrofuran, diethyl ether, MTBE (methyl t-butyl ether), toluene, benzene, pentane, hexane, dioxane or a mixture of said solvents. The process as recited above, wherein the temperature range is about –78° C. to about –20° C., and preferably about –78° C. to about –50° C.

An embodiment of this invention is the process for the preparation of a compound of formula I:

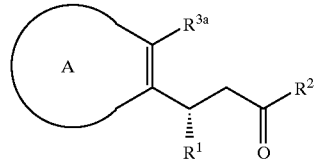

wherein

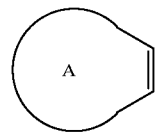

represents:

a) 5- or 6-membered heterocyclyl containing one, two or three double bonds, but at least one double bond and 1, 2 or 3 heteroatoms selected from O, N and S, the heterocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, b) 5- or 6-membered carbocyclyl containing one or two double bonds, but at least one double bond, the carbocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, c) aryl, wherein aryl is as defined below, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, $CO(CH_2)_nCH_3$, and $CO(CH_2)_nCH_2N(R^5)_2$, aryl is defined as phenyl or naphthyl, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$, and when two substituents are located on adjacent carbons they can join to form a 5- or 6-membered ring with one, two or three heteroatoms selected from O, N, and S, which is unsubstituted or substituted with one, two or three substituents selected from the group consisting of: H, OH, $CO_2R^6$, Br, Cl, F, I, $CF_3$, $N(R^7)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, n is 0 to 5;

$R^1$ is:
  a) $C_1$–$C_8$ alkyl, $C_2$–$C_8$ alkenyl, $C_2$–$C_8$ alkynyl, $C_3$–$C_8$ cycloalkyl,
  b) aryl, or
  c) heteroaryl;
    heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, $R^2$ is $OR^4$ or $N(R^5)_2$;

$R^3$ is 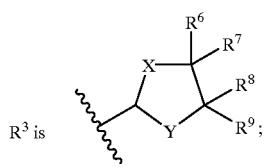

$R^{3a}$ is:
  a) CHO,
  b) —CO-$C_1$–$C_8$ alkyl,
  c) —CO-aryl, or
  d) —CO-heteroaryl;

X and Y are independently: O, S, or $NR^5$;

$R^4$ is $C_1$–$C_8$ alkyl;

$R^5$ is: $C_1$–$C_8$ alkyl, or aryl; and $R^6$, $R^7$, $R^8$ and $R^9$ are independently: H, $C_1$–$C_8$ alkyl, and aryl, such that either $R^6$ and $R^7$ are not the same and/or $R^8$ and $R^9$ are not the same, or $R^6$ and $R^8$ or $R^7$ and $R^9$ can join to form a 5- or 6-membered ring, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$;

comprising the steps of:
1) reacting an α,β-unsaturated ester or amide

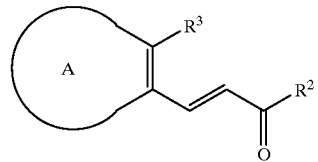

with an organolithium compound, $R^1Li$, in the presence of an aprotic solvent at a temperature range of about −78° C. to about 0° C. to give the conjugate adduct; and 2) removing the chiral auxiliary, $R^3$, with aqueous acid and tetrahydrofuran to give the compound of Formula I.

The process as recited above, wherein the number of equivalents of the organolithium compound, $R^1Li$, is 1 to about 4. The process as recited above, wherein the aprotic solvent is selected from the group consisting of tetrahydrofuran, diethyl ether, MTBE (methyl t-butyl ether), toluene, benzene, hexane, pentane, dioxane or a mixture of said solvents. The process as recited above, wherein the temperature range is about −78° C. to about −20° C., and preferably about −78° C. to about −50° C. The process as recited above, wherein the aqueous acid is aqueous acetic acid.

An embodiment of this invention is the process for the preparation of an aldehyde

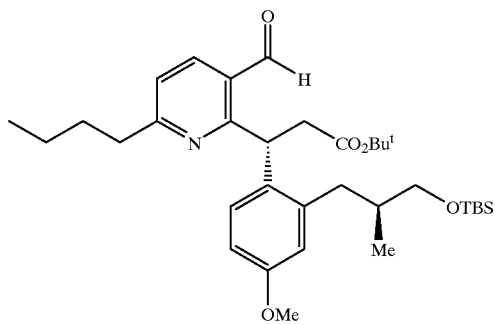

comprising reacting an α,β-unsaturated ester or amide

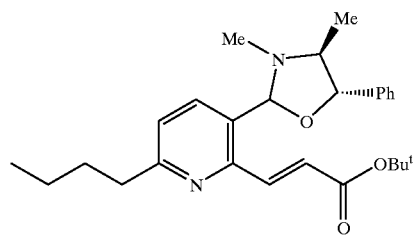

with an organolithium compound

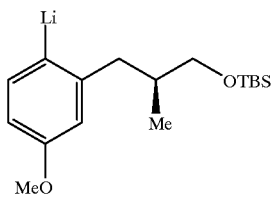

in the presence of an aprotic solvent at a temperature range of about −78° C. to about −20° C.

The process as recited is above, wherein the number of equivalents of the organolithium compound, $R^1Li$, is 1 to about 4 and preferably is 1.5 to about 2.5 equivalents. The process as recited above, wherein the aprotic solvent is selected from the group consisting of tetrahydrofuran, diethyl ether, methyl t-butyl ether (MTBE), toluene, benzene, hexane, pentane, dioxane or a mixture of said solvents, and the preferable aprotic solvent is tetrahydrofuran. The process as recited above, wherein the preferred temperature range is about −78° C. to about −50° C. and a more preferred range is about −78° C. to about −70° C.

A second embodiment of this invention is the process for the preparation of a ketone of formula:

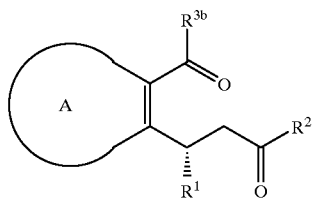

wherein

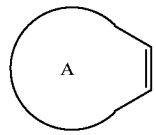

represents:
a) 5- or 6-membered heterocyclyl containing one, two or three double bonds, but at least one double bond and 1, 2 or 3 heteroatoms selected from O, N and S, the heterocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$,
b) 5- or 6-membered carbocyclyl containing one or two double bonds, but at least one double bond, the carbocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$,
c) aryl, wherein aryl is as defined below,
$C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, $CO(CH_2)_nCH_3$, and $CO(CH_2)_nCH_2N(R^5)_2$,
aryl is defined as phenyl or naphthyl, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$, and when two substituents are located on adjacent carbons they can join to form a 5- or 6-membered ring with one, two or three heteroatoms selected from O, N, and S, which is unsubstituted or substituted with one, two or three substituents selected from the group consisting of: H, OH, $CO_2R^6$, Br, Cl, F, I, $CF_3$, $N(R^7)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$,
n is 0 to 5;

$R^1$ is:
a) $C_1$–$C_8$ alkyl, $C_2$–$C_8$ alkenyl, $C_2$–$C_8$ alkynyl, $C_3$–$C_8$ cycloalkyl,
b) aryl, or
c) heteroaryl;
heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, $R^2$ is $OR^4$ or $N(R^5)_2$;

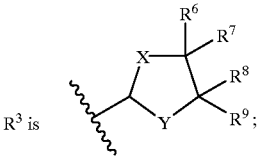

$R^{3b}$ is:
a) $C_1$–$C_8$ alkyl,
b) aryl, or
c) heteroaryl;
X and Y are independently: O, S, or $NR^5$;
$R^4$ is $C_1$–$C_8$ alkyl;
$R^5$ is: $C_1$–$C_8$ alkyl, or aryl; and
$R^6$, $R^7$, $R^8$ and $R^9$ are independently: H, $C_1$–$C_8$ alkyl, and aryl, such that either $R^6$ and $R^7$ are not the same and/or $R^8$ and $R^9$ are not the same, or $R^6$ and $R^8$ or $R^7$ and $R^9$ can join to form a 5- or 6-membered ring, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$;

comprising the steps of:

1) reacting a α,β-unsaturated ester or amide

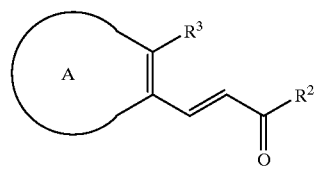

with an organolithium compound, $R^1Li$, in the presence of an aprotic solvent at a temperature range of about −78° C. to about 0° C. to give a conjugate adduct

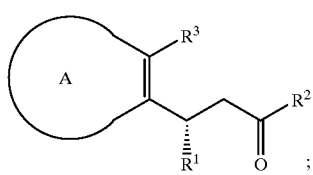

2) removing the chiral auxiliary with aqueous acid and tetrahydrofuran to give the aldehyde

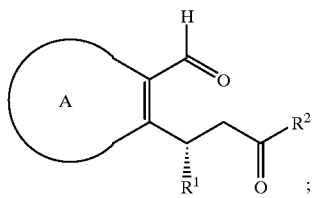

3) reacting the aldehyde with a Grignard reagent or organolithium reagent formed with $R^{3b}Z$, where Z is Br, Cl, or I to form an alcohol

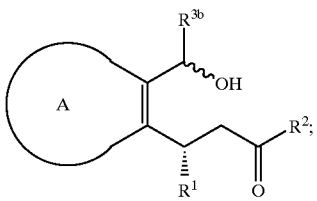

4) oxidizing the alcohol formed with an oxidizing agent to give the ketone

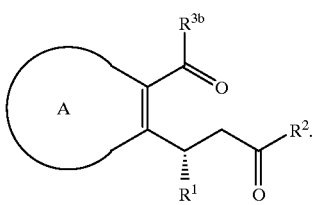

The process as recited above, wherein the number of equivalents of the organolithium compound, $R^1Li$, in the first step is 1 to about 4. The process as recited above, wherein the aprotic solvent in the first step is selected from the group consisting of tetrahydrofuran, diethyl ether, methyl t-butyl ether, toluene, benzene, pentane, hexane, dioxane or a mixture of said solvents. The process as recited above, wherein the temperature range in the first step is about $-78°$ C. to about $-70°$ C.

The process as recited above, wherein the aqueous acid in the second step is aqueous acetic acid.

The process as recited above, wherein the oxidizing agent in the forth step is 4-methylmorpholine-N-oxide (NMO) and tetrapropylammonium perruthenate(VII) (TPAP).

A second embodiment of this invention is the process for the preparation of a ketone of formula:

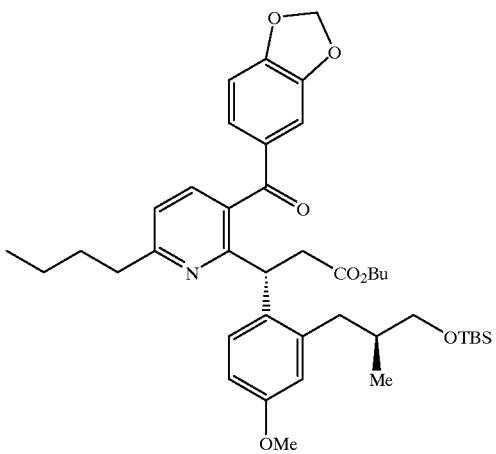

comprising the steps of:

1) reacting a $\alpha,\beta$-unsaturated ester or amide

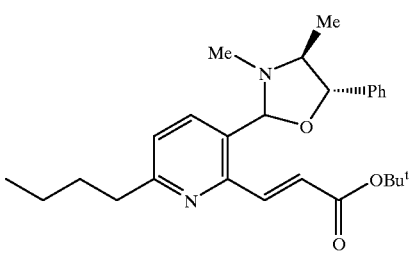

with an organolithium compound

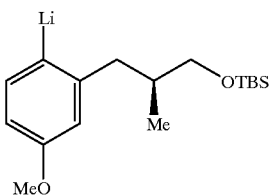

in the presence of an aprotic solvent at a temperature range of about $-78°$ C. to about $0°$ C. to give a conjugate adduct

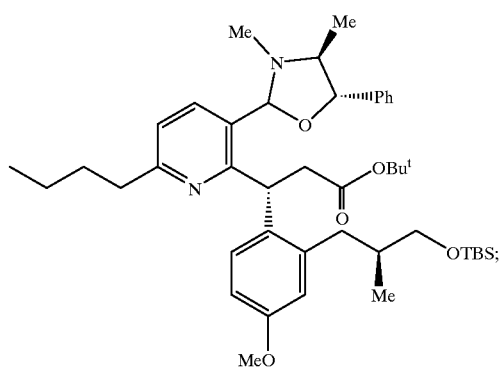

2) removing the chiral auxiliary with aqueous acid and tetrahydrofuran to give the aldehyde

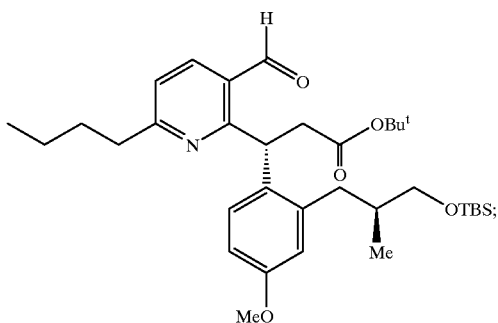

3) reacting the aldehyde with a Grignard reagent or organolithium reagent formed with

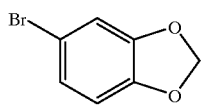

to form an alcohol

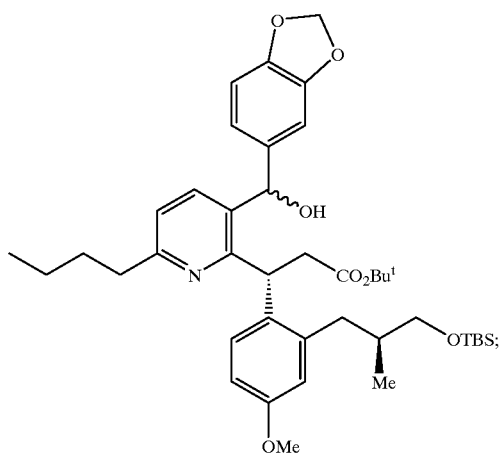

4) oxidizing the alcohol formed with an oxidizing agent to give a ketone

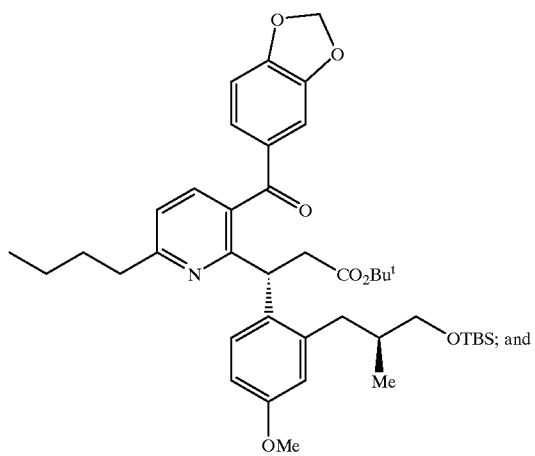

5) transesterifying the ester with n-butanol and a Lewis acid to give the desired n-butyl ester.

The process as recited above, wherein the number of equivalents of the organolithium compound, $R^1Li$, in the first step is 1 to about 4. The process as recited above, wherein the aprotic solvent in the first step is selected from the group consisting of tetrahydrofuran, diethyl ether, methyl t-butyl ether, toluene, benzene, pentane, hexane, dioxane or a mixture of said solvents. The process as recited above, wherein the temperature range in the first step is about −78° C. to about −50° C.

The process as recited above, wherein the aqueous acid in the second step is aqueous acetic acid.

The process as recited above, wherein the Grignard reagent or organolithium reagent in the third step are

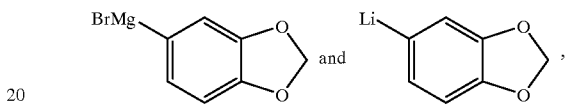

respectively.

The process as recited above, wherein the oxidizing agent in the forth step is 4-methylmorpholine-N-oxide (NMO) and tetrapropylammonium perruthenate(VII) (TPAP).

The process as recited above, wherein the fifth step is conducted in the presence of a Lewis acid selected from $Ti(OEt)_4$, $Ti(OiPr)_4$, or $Ti(OBu)_4$.

It is further understood that the substituents recited above would include the definitions recited below.

The alkyl substituents recited above denote straight and branched chain hydrocarbons of the length specified such as methyl, ethyl, isopropyl, isobutyl, tert-butyl, neopentyl, isopentyl, etc.

The alkenyl-substituents denote alkyl groups as described above which are modified so that each contains a carbon to carbon double bond such as vinyl, allyl and 2-butenyl.

Cycloalkyl denotes rings composed of 3 to 8 methylene groups, each of which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

The heteroaryl substituent represents an carbazolyl, furanyl, thienyl, pyrrolyl, isothiazolyl, imidazolyl, isoxazolyl, thiazolyl, oxazolyl, pyrazolyl, pyrazinyl, pyridyl, pyrimidyl, purinyl.

The heterocyclyl substituent represents a pyridyl, pyrimidyl, thienyl, furanyl, oxazolidinyl, oxazolyl, thiazolyl, isothiazolyl, pyrazolyl, triazolyl, imidazolyl, imidazoldinyl, thiazolidilnyl, isoxazolyl, oxadiazolyl, thiadiazolyl, morpholinyl, piperidinyl, piperazinyl, pyrrolyl, or pyrrolidinyl.

The α,β-unsaturated ester or amide

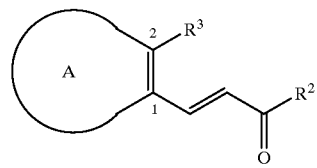

can generally be prepared in two steps:

1) a coupling reaction at the one position of Ring A

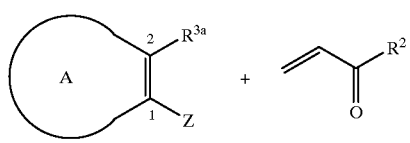

wherein Z is a leaving such as Br, Cl, I, OTriflyl, OTosyl or OMesyl and $R^2$ is $OR^4$ or $N(R^5)_2$; and 2) the conversion of the aldehyde ($R^{3a}$=CHO) to the desired chiral auxiliary ($R^3$), wherein $R^3$ represents

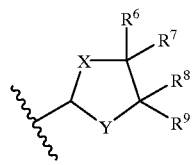

X and Y are independently: O, S, or $NR^5$; $R^4$ is $C_1$–$C_8$ alkyl; $R^5$ is: $C_1$–$C_8$ alkyl, or aryl; and $R^6$, $R^7$, $R^8$ and $R^9$ are independently: H, $C_1$–$C_8$ alkyl, and aryl, such that either $R^6$ and $R^7$ are not the same and/or $R^8$ and $R^9$ are not the same, or $R^6$ and $R^8$ or $R^7$ and $R^9$ can join to form a 5- or 6-membered ring, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$.

Commercially available pyridone 1 is alkylated via its dianion with propyl bromide, and the product is then converted into the bromopyridine 3a using a brominating agent such as $PBr_3$. The nitrile 3a is then reduced to the aldehyde 3 using diisobutyl aluminum hydride (DIBAL). The aldehyde then undergoes a Heck reaction with t-butyl acrylate using NaOAc, $(allyl)_2PdCl_2$, tri-o-tolylphosphine, toluene, reflux to provide the unsaturated ester 4a in high yield. The unsaturated ester 4a is then reacted with a chiral auxiliary to give the acceptor 5a. Examples of chiral auxiliaries useful in this method are the enantiomers of pseudoephedrine, ephedrine, 1N,2N-dimethyldiaminocyclohexane, diphenylprolinol, N-methylaminoindanol, and 1N,2N-diethyldiaminocyclohexane.

Scheme 1

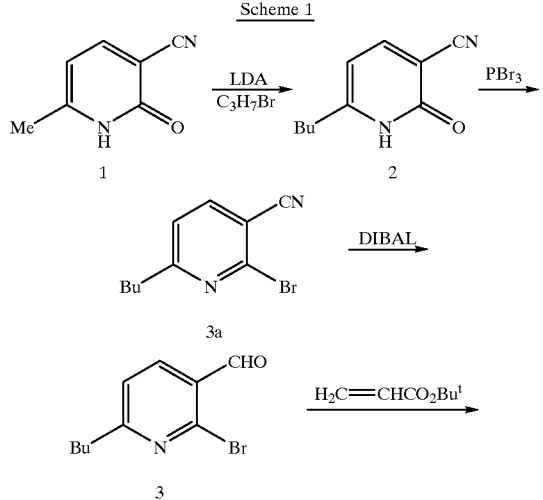

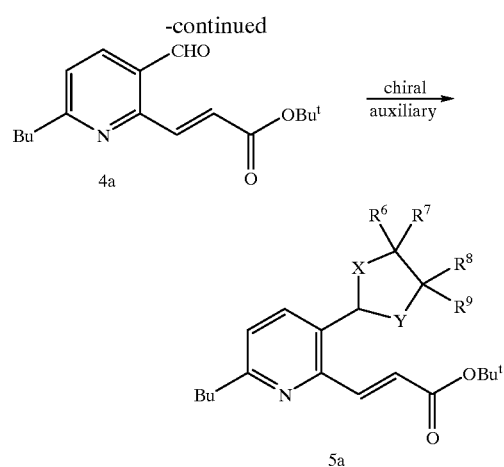

Commercially available acid 10 is reduced with $BH_3.SMe_2$, to the alcohol 11, which is then converted into the bromide 13, via the mesylate 12 using mesyl chloride, triethylamine followed by the addition of NaBr and dimethylacetamide (DMAC).

Scheme 2

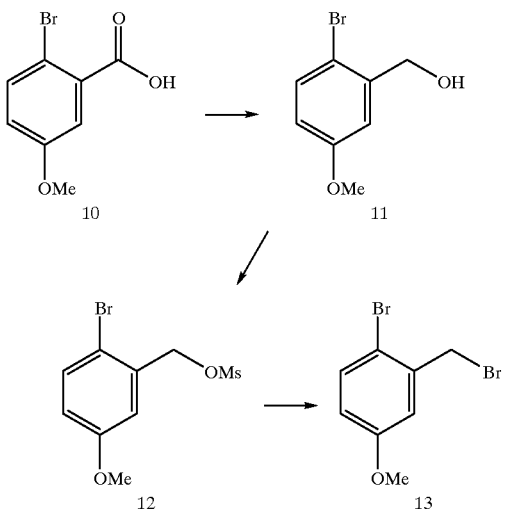

Commercial available 1,2-amino indanol is acylated (propionyl choride, $K_2CO_3$) to give amide 8, which is then converted into the acetonide 9 (2-methoxypropene, pyridinium p-toluene-sulfonate (PPTS)). Acetonide 9 is then alkylated with the bromide 13, (LiHMDS) to give 14, which is then hydrolyzed ($H^+$, MeOH) to give a mixture of acid and methyl ester 15. Reduction (LAH) of the ester/acid mixture provided the alcohol 16 in high yield and optical purity. Protection of the alcohol 16 (TBSCl, imidazole) provided bromide 17, the precursor to organolithium 17a.

Scheme 3

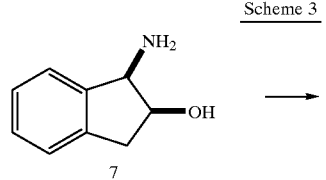

21
-continued

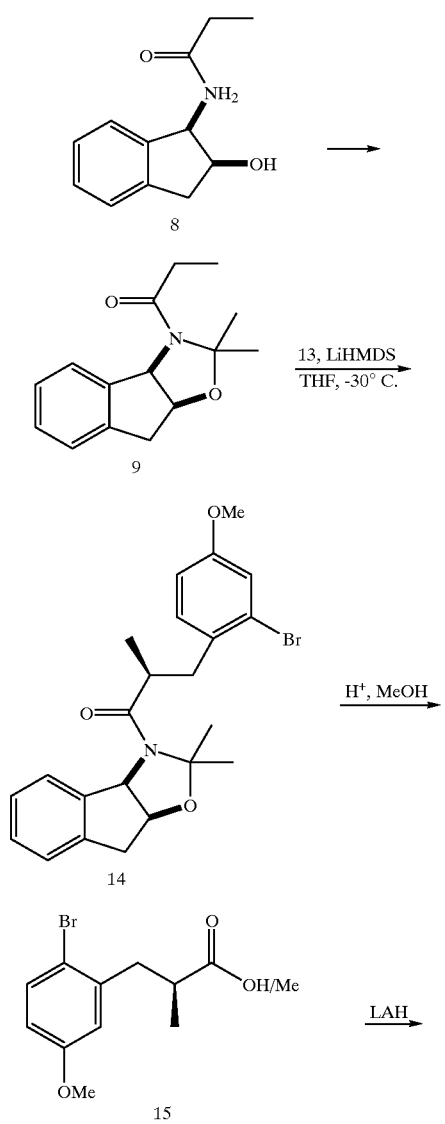

22
-continued

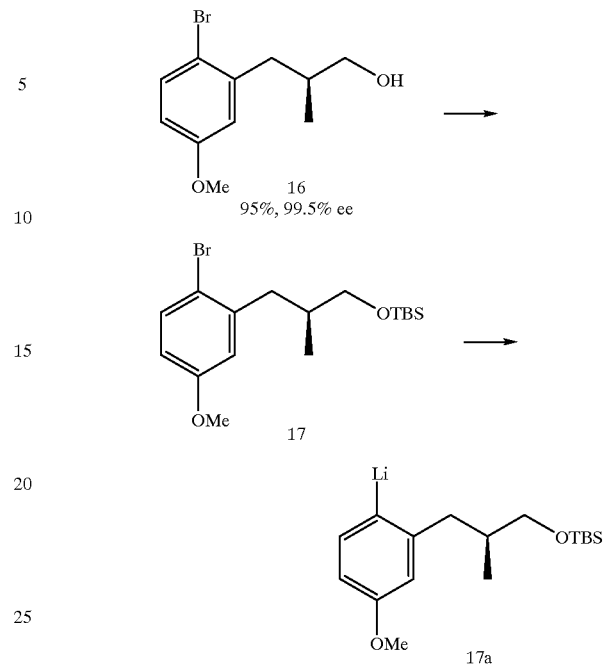

Compound 17a is added to the α,β-unsaturated ester 5a at −78° to −50° C. Work up with acetic acid, THF and water (to remove the auxiliary) affords compound 6a in high yield and good selectivity. Addition of the Grignard leads to compound 18. Oxidation with reagents such as NMO and TPAP with molecular sieves, followed by transesterification in n-butanol with Ti(OBu)$_4$ leads to compound 19 in good yield.

Scheme 4

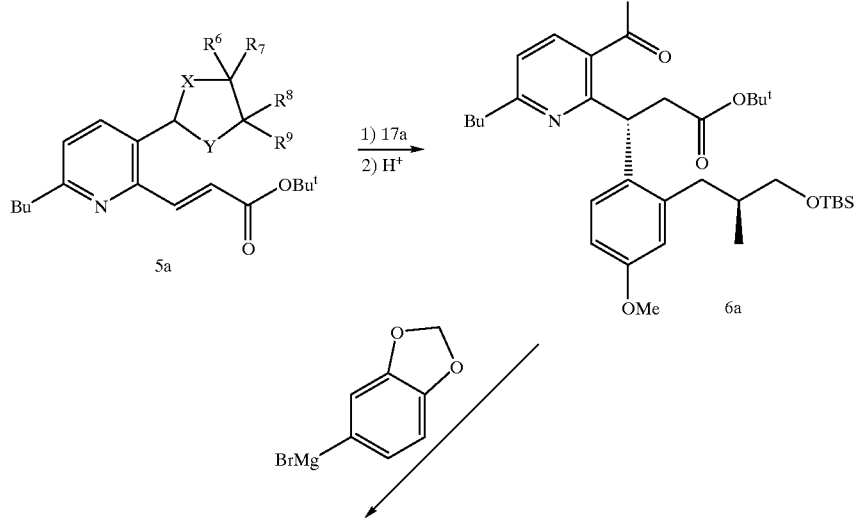

-continued

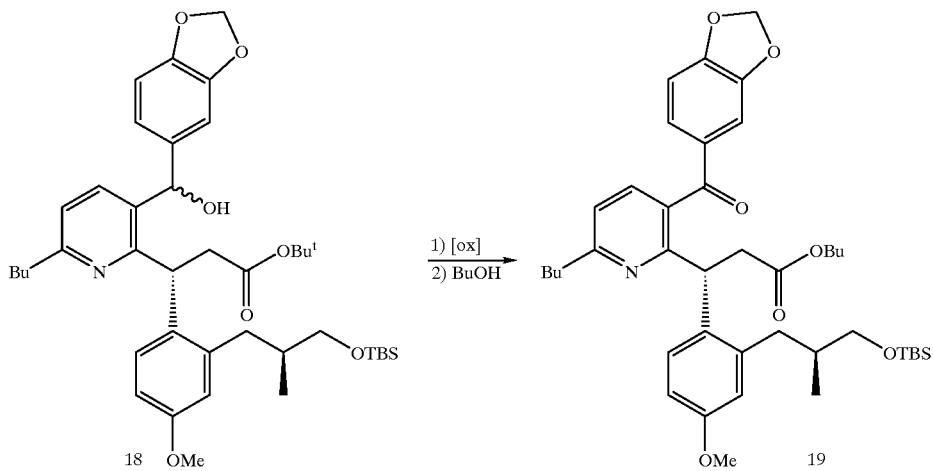

The instant invention can be understood further by the following examples, which do not constitute a limitation of the invention.

EXAMPLE 1

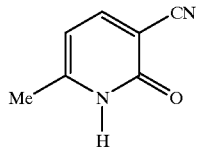

Preparation of 1

Compound 1 is a commercially available starting material, for example, see Aldrich Chemical Company, Milwaukee, Wis., USA 53201.

EXAMPLE 2

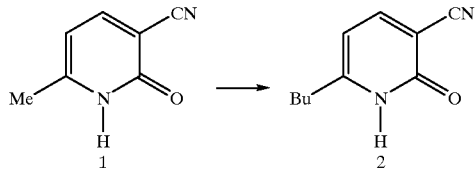

Preparation of 2

Diisopropyl amine (MW 101.19, d 0.772, 2.1 equ, 20.54 mL) in 200 mL THF. Cool to −50° C. and add n-BuLi (1.6 M in hexanes, 2.05 equ, 96 mL), allowing solution to warm to −20° C. Age 0–3° C. for 15 min, then cool to −30° C. and add 1 (MW 134.14, 75 mmol, 10.0 g). Age 0° C. to 43° C. for 2 h. Cool to −50° C. and add bromopropane (MW 123.00, d 1.354, 1.0 equ, 6.8 mL). Warm to 25° C. over 30 min, and age 30 min. Add NH$_4$Cl and CH$_2$Cl$_2$. Dry organic (magnesium sulfate) then evaporate in vacuo to afford 61% of 2.

EXAMPLE 3

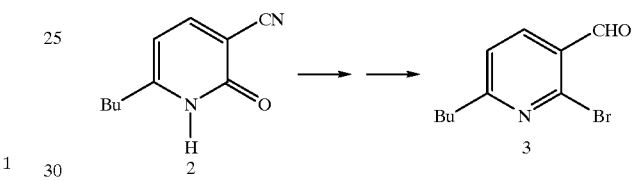

Preparation of 3

Mix 2 (MW 176.22, 46 mmol) and PBr$_3$ (MW 270.70, d 2.880, 2.5 equ, 10.8 mL) and age at 160° C. After 2 h, cool to 25° C. and add some CH$_2$Cl$_2$. Slowly quench by adding water. Separate layers and wash aqueous two times with CH$_2$Cl$_2$. Combine organic layers and dry (magnesium sulfate). Concentrate and isolate solid by silica gel chromatography (90:10 hexanes:ethyl acetate) in 60% yield (MW 239.12, 6.60 g).

Dissolve product of bromination reaction (MW 239.12, 27.6 mmol, 6.60 g) in 66 mL toluene and cool to −42° C. Slowly add DIBAL (1.5 M in toluene, 2 equ, 37 mL) and age 1 h at −42° C. Add HCl (2 N, 10 equ, 134 mL) and stir vigorously for 30 min. Dilute with ethyl acetate, separate layers, and wash aqueous with ethyl acetate. Combine organic layers, dry (magnesium sulfate), and concentrate in vacuo to afford 90% (MW 242.11, 6.01 g) of 3.

EXAMPLE 4a

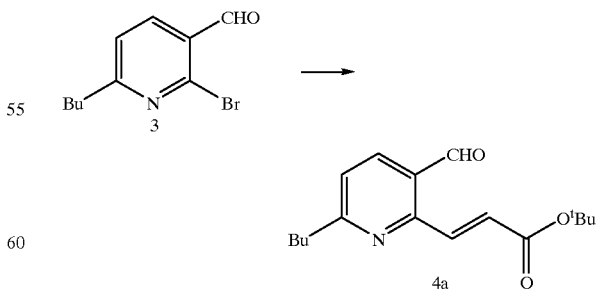

Preparation of 4a

Dissolve 3 (MW 242.11, 24.8 mmol, 6.01 g) in 75 mL toluene. Add sodium acetate (MW 82, 3 equ, 6.13 g), t-butyl acrylate (MW 128.17, d 0.875, 2.5 equ, 9.08 mL), P(o-

EXAMPLE 4b

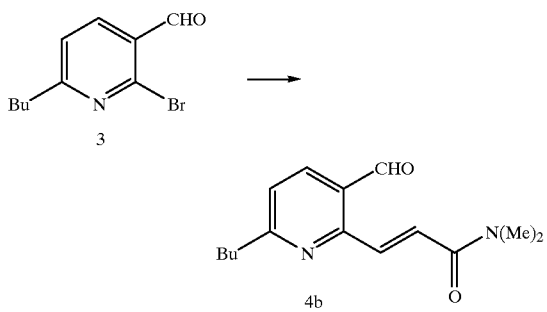

Preparation of 4b

Dissolve 3 (MW 242.11, 24.8 mmol, 6.01 g) in 75 mL toluene. Add sodium acetate (MW 82, 3 equ, 6.13 g), dimethylacrylamide (MW 99.13, d 0.962, 1 equ, 2.55 mL), PPh$_3$ (MW 262.29, 10 mol %, 653 mg) and allyl palladium chloride dimer (MW 365.85, 5 mol %, 455 mg). Age at 140° C. in sealed tube for 24 h. Cool, filter and evaporate in vacuo. Isolate 4b (MW 260.34) by silica gel chromatography (80:20 hexanes:ethyl acetate) in 70% yield (4.52 g).

EXAMPLE 5a

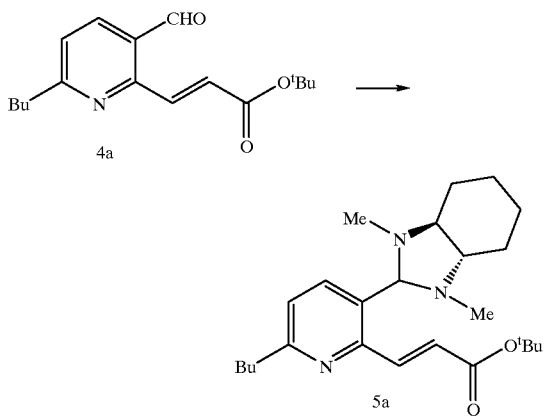

Preparation of 5a

Dissolve 4a (MW 289.37, 19.8 mmol, 5.74 g) in 53 mL CH$_2$Cl$_2$. Add (1R,2R)-N,N-dimethylcyclohexanediamine (MW 142.24, 1 equ, 2.83 g) and sieves (powdered, 1 wt equ, 5.74 g) and age 25° C. for 8 h. Filter and concentrate filtrate in vacuo to afford 5a (MW 413.60, 8.19 g) in quantitative yield.

tolyl)$_3$ (MW 304.38, 10 mol %, 755 mg) and allyl palladium chloride dimer (MW 365.85, 5 mol %, 455 mg). Age at reflux for 24 h. Cool, filter and evaporate in vacuo. Isolate 4a (MW 289.37) by silica gel chromatography (92:8 hexanes:ethyl acetate) in 80% yield (5.74 g).

EXAMPLE 5b

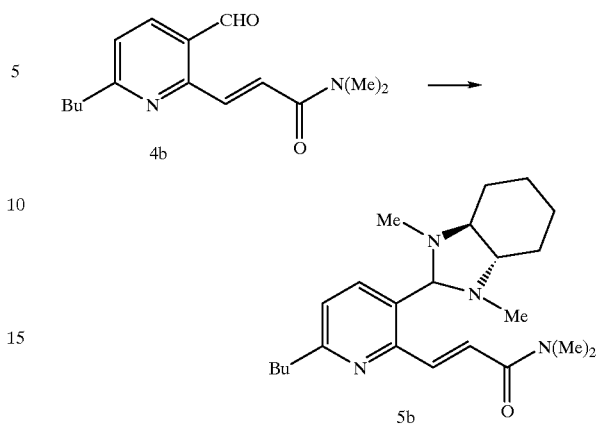

Preparation of 5b

Dissolve 4b (MW 260.34, 17.4 mmol, 4.53 g) in 40 mL CH$_2$Cl$_2$. Add (1R,2R)-N,N-dimethylcyclohexanediamine (MW 142.24, 1 equ, 2.47 g) and sieves (powdered, 1 wt equ, 4.53 g) and age 25° C. for 8 h. Filter and concentrate filtrate in vacuo to afford 5b (MW 384.57, 6.69 g) in quantitative yield.

EXAMPLE 5c

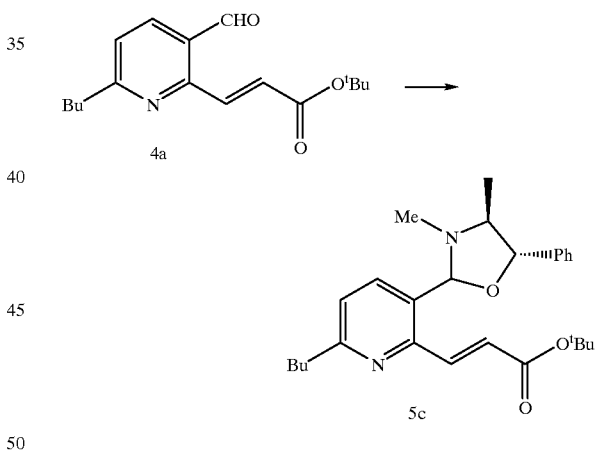

Preparation of 5c

Dissolve 4a (MW 289.37, 19.8 mmol, 5.74 g) in 53 mL toluene. Add (S,S)-pseudoephedrine (MW 165.24, 1.1 equ, 3.60 g) and 4 drops of concentrated HCl. Reflux with a Dean-Stark trap for 2 h. Wash with saturated aqueous NaHCO$_3$ and extract with ethyl acetate. Dry organic layer with MgSO$_4$, then filter and concentrate filtrate in vacuo to afford 5c (MW 4436.59, 8.64 g) in quantitative yield.

$^1$H NMR (CDCl$_3$): 8.23 (d, J=11.78, 1 H), 7.88 (d, J=7.33, 1 H), 7.39 (m, 5 H), 7.16 (d, J=7.33, 1 H), 7.02 (d, J=11.78, 1 H), 5.31 (s, 1 H), 4.80 (d, J=9.18, 1 H), 2.80 (t, J=5.79, 2 H), 2.59 (m, 1 H), 2.19 (s, 3 H), 1.72 (m, 2 H), 1.56 (s, 9 H), 1.39 (m, 2 H), 1.27 (d, J=4.33, 3 H), 0.94 (t, J=6.76, 3 H).

EXAMPLE 5d

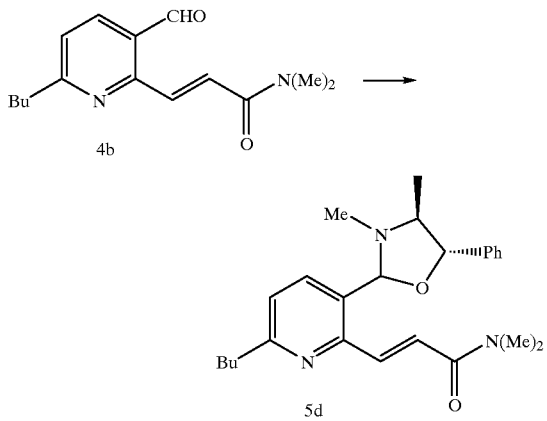

Preparation of 5d

Dissolve 4b (MW 260.34, 117.4 mmol, 5.74 g) in 53 mL toluene. Add (S,S)-pseudoephedrine (MW 165.24, 1.1 equ, 3.16 g) and 4 drops of concentrated HCl. Reflux with a Dean-Stark trap for 2 h. Wash with saturated aqueous NaHCO$_3$ and extract with ethyl acetate. Dry organic layer with MgSO$_4$, then filter and concentrate filtrate in vacuo to afford 5c.

EXAMPLE 6a

Preparation of 6a

Dissolve 17 (see Example 17, MW 373.41, 2 equ, 14.79 g) in 85 mL THF. Cool to −78° C. and add t-BuLi (1.7 M in pentane, 4 equ, 46.6 mL), maintaining temperature below −70° C. Age 15 min, then slowly add solution of 5c (MW 436.59, 19.8 mmol, 8.64 g) in 65 mL THF. Age 1 h at −78° C., then cannula into cold aq NH$_4$Cl (100 mL). Add ethyl acetate and separate layers. Wash aqueous with ethyl acetate. Combine organic layers and wash with brine, then dry (magnesium sulfate) and evaporate in vacuo. $^1$H NMR provides de data. Add THF (75 mL), acetic acid (AcOH) (30 mL) and water (10 mL). Age 5 h at 25° C. Separate layers and wash aqueous two times with ethyl acetate. Combine organic layers, wash with brine, dry (magnesium sulfate), and evaporate in vacuo. 6a (MW 583.89) is isolated in 85% yield (9.83 g) by silica gel chromatography (92:8 hexanes-:ethyl acetate).

$^1$H NMR (C$_6$D$_6$): 10.5 (s, 1 H), 7.72 (d, J=7.85, 1 H), 7.30 (d, J=8.64, 1 H), 6.83 (d, J=8.05, 1 H), 6.59 (dd, J=8.65, 2.61, 1 H), 6.56 (d, J=7.99, 1 H), 5.92 (m, 1 H), 3.85 (dd, J=16.32, 10.77, 1 H), 3.48 (m, 2 H), 3.32 (s, 3 H), 3.01 (dd, J=14.11, 6.77, 1 H), 2.87 (dd, J=16.30, 3.91, 1 H), 2.79 (dd, J=13.25, 6.21, 1 H), 2.68 (t, J=7.66, 2 H), 2.10 (m, 1 H), 1.72 (m, 2 H), 1.30 (s, 9 H), 1.25 (m, 2 H), 1.01 (s, 9 H), 0.95 (d, J=6.42, 3 H), 0.94 (t, J=8.40, 3 H), 0.10 (d, J=5.83, 6 H).

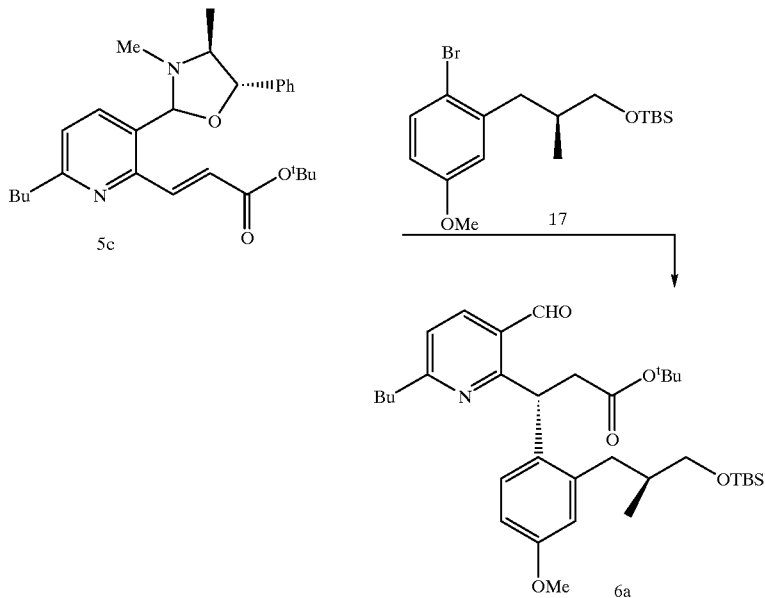

EXAMPLE 6b

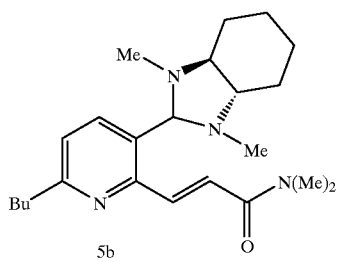
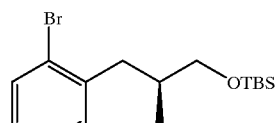

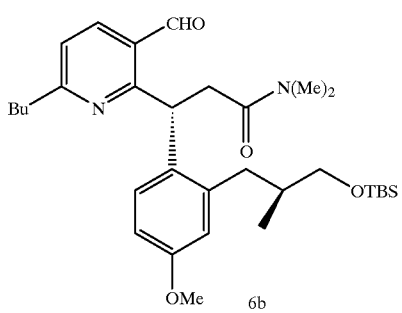

Preparation of 6b

Dissolve 17 (see Example 17, MW 373.41, 2 equ, 12.99 g) in 70 mL THF. Cool to −78° C. and add t-BuLi (1.7 M in pentane, 4 equ, 40.9 mL), maintaining temperature below −70° C. Age 15 min, then slowly add solution of 5b (MW 384.57, 17.4 mmol, 6.69 g) in 55 mL THF. Age 1 h at −78° C., then cannula into cold aq $NH_4Cl$ (100 mL). Add ethyl acetate and separate layers. Wash aqueous with ethyl acetate. Combine organic layers and wash with brine, then dry (magnesium sulfate) and evaporate in vacuo. $^1H$ NMR provides de data. Add THF (55 mL), AcOH (20 mL) and water (8 mL). Age 5 h at 25° C. Separate layers and wash aqueous two times with ethyl acetate. Combine organic layers, wash with brine, dry (magnesium sulfate), and evaporate in vacuo. 6b (MW 678.99) is isolated in 75% yield (8.86 g) by silica gel chromatography (70:30 hexanes:ethyl acetate).

$^1H$ NMR ($CDCl_3$): 10.30 (s, 1 H), 7.99 (d, J=4.74, 1 H), 7.11 (d, J=3.19, 1 H), 6.89 (d, J=9.61, 1 H), 6.78 (d, J=2.76, 1 H), 6.59 (t, J=2.78, 1 H), 5.70 (t, J=2.86, 1 H), 3.87 (dd, J=11.18, 4.29, 1 H), 3.74 (s, 3 H), 3.58 (m, 2 H), 3.11 (s, 3 H), 3.25 (dd, J=14.35, 6.25, 1 H), 2.88 (s, 3 H), 2.84 (m, 2H), 2.68 (dd, J=14.35, 8.30, 1 H), 2.47 (dd, J=9.02, 2.89, 1 H), 2.09 (m, 1 H), 1.75 (m, 2 H), 1.39 (m, 2 H), 0.99 (t, J=3.49, 3 H), 0.92 (s, 9 H), 0.92 (d, J=7.15, 6 H), 0.08 (d, J=1.91, 6 H).

$^{13}C$ NMR ($CDCl_3$): 190.5, 171.6, 165.9, 163.7, 157.9, 139.3, 137.2, 135.5, 130.0, 127.1, 120.8, 115.5, 111.7, 67.8, 55.11, 39.7, 38.9, 38.4, 37.2, 36.8, 36.0, 35.4, 26.0 (3 C), 22.3, 18.4, 17.3, 14.7, −5.3 (2 C).

EXAMPLE 7

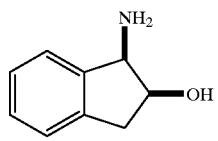

Preparation of 7

Compound 7 is a commercially available starting material, for example, see DSM Andeno, Grubbenvorsterweg 8, P.O. Box 81, 5900 AB Venlo, The Netherlands.

EXAMPLE 8

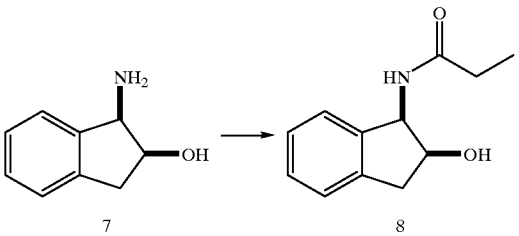

Preparation of 8

$Na_2CO_3$ (MW 105.99, 1.5 equ, 8.8 g) dissolved in 82 mL water. Add a solution of (1R,2S) amino indanol 7 (MW 149.19, 55.0 mmol, 8.2 g) in 160 mL $CH_2Cl_2$. Cool to −5° C. and add propionyl chloride (MW 92.53, d 1.065, 1.3 equ, 6.2 mL). Warm to 25° C. and age 1 h. Separate layers and dry organic (magnesium sulfate). Concentrate in vacuo to afford 8 (MW 205.26, 10 g) In 89% isolated yield.

EXAMPLE 9

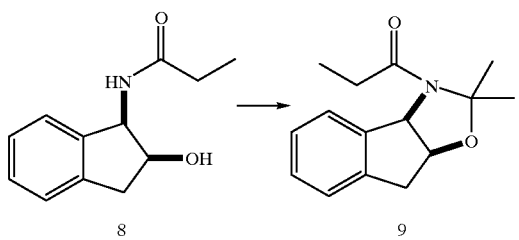

Preparation of 9

To a solution of 8 (MW 205.26, 49.3 mmol, 10 g) in 200 mL THF, add pyridinium p-toluenesulfonate (PPTS) (MW 251.31, 0.16 equ, 2 g) then methoxypropene (MW 72.11, d 0.753, 2.2 equ, 10.4 mL). Age 2 h at 38° C., then add aqueous sodium bicarbonate and ethyl acetate. The organic layer was dried (magnesium sulfate). After concentration in vacuo, 9 (MW 245.32, 12.09 g) was formed in quantitative yield.

EXAMPLE 10

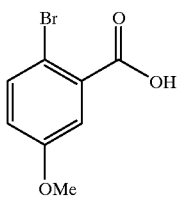

Preparation of 10

Compound 10 is a commercially available starting material, for example, see Lancaster Synthesis, P.O. Box 1000, Windham, N.H. 03087-9977 or Ryan Scientific, Inc., P.O. Box 845, Isle of Palms, S.C. 29451-0845.

EXAMPLE 11

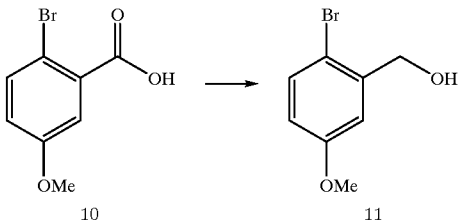

Preparation of 11

10 (MW 231.05, 130 mmol, 30.0 g) in 300 mL CH$_2$Cl$_2$ at 0° C. Add BH$_3$-SMe$_2$ (3 equ, 25.2 mL) and age for 2 h at 25° C. Quench into aqueous 2 N HCl and separate layers. Dry organic (magnesium sulfate) and concentrate in vacuo to obtain 94% yield of 11 (MW 217.06, 25.5 g).

EXAMPLE 12

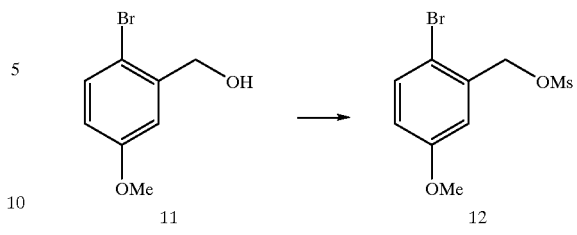

Preparation of 12

Dissolve 11 (MW 217.06, 47.2 mmol, 10.24 g) in 55 mL CH$_2$Cl$_2$ and cool to −20° C. Add DIEA (MW 129.25, d 0.742, 1.3 equ, 10.69 mL) then methane sulfonyl chloride (MsCl) (MW 114.55, d 1.480, 1.2 equ, 4.38 mL). Age −5° C. to 0° C. for 1 h then quench into 55 mL water. Extract with CH$_2$Cl$_2$ then wash with 1N H$_2$SO$_4$ (40 mL), then brine. Dry organic layers (magnesium sulfate) and concentrate in vacuo to afford 12 (MW 295.15, 13.23 g) in 95% yield.

EXAMPLE 13

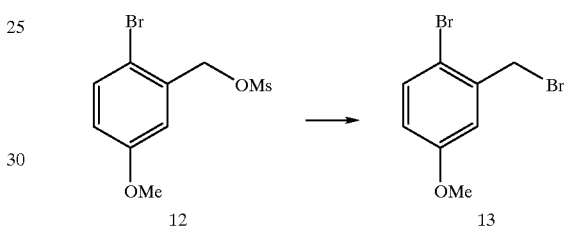

Preparation of 13

12 (MW 295.15, 44.8 mmol, 13.23 g) in 44 mL dimethylacetamide (DMAC). Add NaBr (MW 102.90, 2 equ, 9.22 g) and age 1 h. Add 88 mL water and collect solid by filtration. Wash cake with water and dry by suction. Quantitative yield of 13 (MW 279.96, 12.54 g) is obtained.

EXAMPLE 14

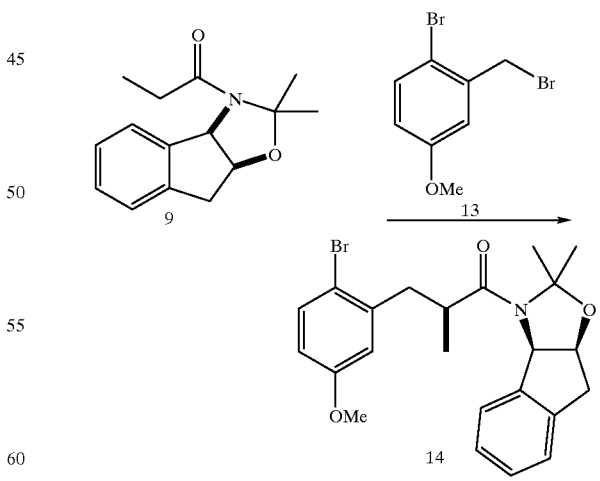

Preparation of 14

9 (MW 245.32, 1.1 equ, 89.1 g) in 1 L THF, cooled to −50° C. Add LiHMDS (1.0 M in THF, 1.5 equ, 545 mL) and age 1.5 h, warming to −30° C. Add 13 (MW 279.96, 327 mmol, 91.3 g) in 300 mL THF, and age −35° C. for 1 h.

Warm to −10° C. over 1 h, then quench into aqueous NH₄Cl. Separate layers and extract with ethyl acetate. Dry organic and concentrate in vacuo to afford crude 14 (MW 444.37).

EXAMPLE 15

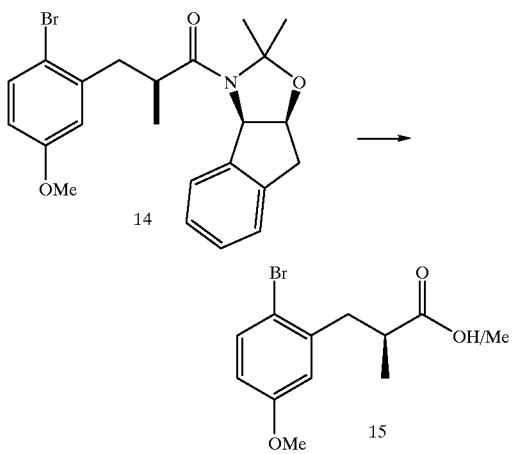

Preparation of 15

14 in 1 L MeOH and cooled to 10° C. Bubble in HCl gas for 1 h until reaction is complete. 2 L H₂O added and the product was filtered. The cake was washed with H₂O and dried to give the product hydroxyamide, which was then dissolved in 1 L MeOH and 1.5 L 6N HCl and refluxed overnight. The mixture was cooled to 25° C. and extracted with CH₂Cl₂ to give, after concentration, compounds 15 (60 g, 64% from bromide 13).

EXAMPLE 16

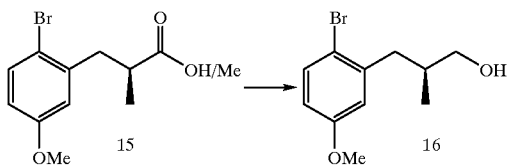

Preparation of 16

15 (mixture of acid and ester, 26.88 mmol) in 150 mL THF at −78° C. Add lithium aluminum hydride (LiAlH₄) (1 M in THF, 2 equ, 53.76 mL) over 30 min. Warm to 25° C. over 1 h, then quench into aqueous NH₄Cl. Add ethyl acetate, extract ethyl acetate. Wash organics with brine, dry (magnesium sulfate), and concentrate in vacuo to afford 95% yield of 16 (MW 259.14, 6.62 g).

EXAMPLE 17

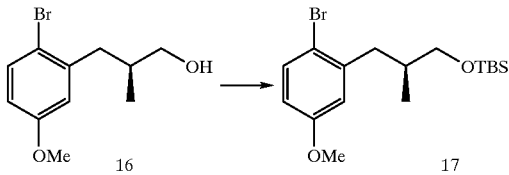

Preparation of 17

16 (MW 259.14, 25.54 mmol, 6.62 g) in 35 mL CH₂Cl₂ and cool to 0° C. Add imidazole (MW 68.08, 2.5 equ, 4.35 g) and then tert-butyldimethylsilyl chloride (TBSCl) (MW 150.73, 1 equ, 3.85 g). Age 1 h at 25° C. then quench with aqueous NaHCO₃ and add ethyl acetate. Extract with ethyl acetate, then dry organic layer (magnesium sulfate) and concentrate in vacuo to afford a quantitative yield of 17 (MW 373.41, 9.54 g).

$^1$H NMR (CDCl₃): 7.41 (d, J=8.74, 1 H), 6.77 (d, J=3.04, 1 H), 6.63 (dd, J=8.73, 3.06, 1H), 3.78 (s, 3 H), 3.50 (d, J=5.75, 2 H), 2.89 (dd, J=13.31, 6.15, 1 H), 2.45 (dd, J=13.30, 8.26, 1 H), 2.03 (m, 1 H), 0.94 (s, 9 H), 0.92 (d, J=5.01, 3 H), 0.07 (s, 6 H).

$^{13}$C NMR (CDCl₃): 159.1, 141.6, 133.2, 117.0, 115.4, 113.2, 67.4, 55.4, 39.7, 36.3, 26.0 (3C), 18.4, 16.5, −5.3 (2C).

EXAMPLE 18

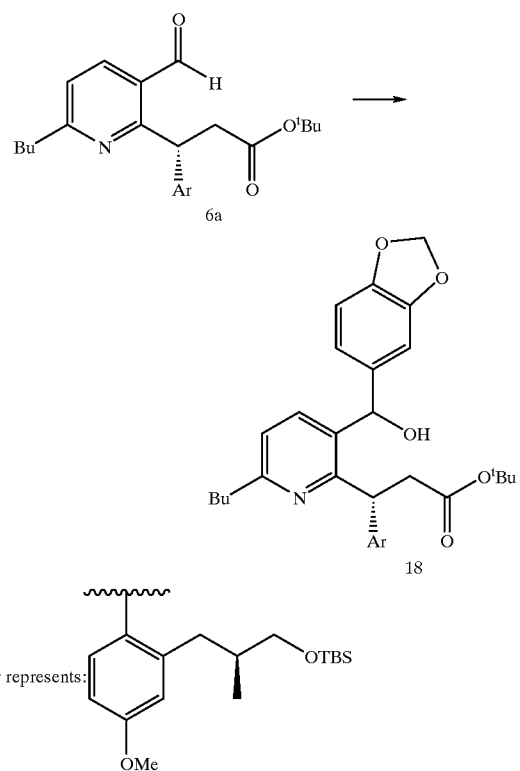

Preparation of 18

Prepare 0.5 M Grignard solution from 4-bromo-1,2-(methylenedioxy)benzene (MW 201.01, 42.1 mmol, 8.46 g) and Mg (MW 24.31, 1.5 equ, 1.54 g) in 84 mL THF. Dissolve 6a (MW 583.89, 16.8 mmol, 9.83 g) in 80 mL THF and cool to −78° C. Slowly add Grignard solution (2.5 equ, 0.5 M, 84 mL) and age 30 min. Quench into aqueous NH₄Cl and add ethyl acetate. Wash organic with brine, dry (magnesium sulfate) and evaporate in vacuo. Carry crude into oxidation.

EXAMPLE 19

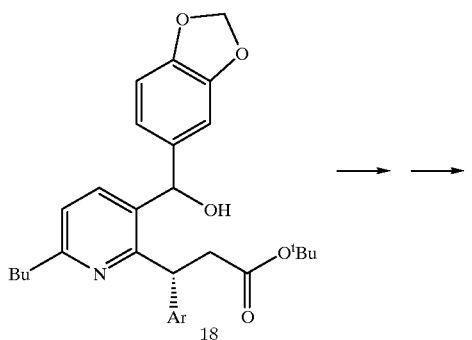

Preparation of 19

Crude 18 (MW 706.01, 16.8 mmol) in 150 mL ACN. Add NMO (MW 117.15, 3 equ, 5.90 g), sieves (powdered, 3 wt equ, 35.6 g), and TPAP (MW 351.43, 10 mol %, 590 mg) and age 25° C. for 2 h. Concentrate to remove ACN, then elute through silica gel pad with ethyl acetate. Concentrate in vacuo, then chromatograph (90:10 hexanes:ethyl acetate) to isolate the oxidation product (85% yield over two steps).

Dissolve in 100 mL n-BuOH and add Ti(OBu)$_4$ (MW 340.366, 5 equ, 28.59 g). Reflux for 48 h, then quench into water and add ethyl acetate. Filter through celite, separate the layers, and wash the organic with brine. Dry (magnesium sulfate) and evaporate in vacuo to afford 81% yield (over three steps) of 19 (MW 703.99, 9.58 g).

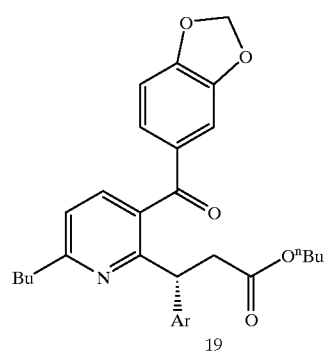

EXAMPLES 20–26

Following the procedures described in Examples 6a and 6b, the nucleophiles were added to the acceptors listed below and the diasteromeric ratios (%de) of the products were determined by evaluation of the $^1$H NMR data and are shown below.

| Ex. | Acceptor | Nucleophile | % de |
|---|---|---|---|
| 20 | ![structure] | ![structure] | 90% |
| 21 | ![structure] | ![structure] | 65% |

-continued

| Ex. | Acceptor | Nucleophile | % de |
|---|---|---|---|
| 22 | | | 88% |
| 23 | | | 50% |
| 24 | | | 76% |
| 25 | | | 92% |
| 26 | | | 88% |

What is claimed is:

1. A process for the preparation of a compound of formula I:

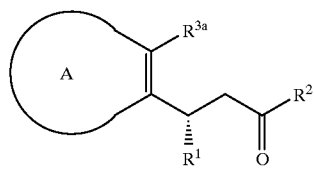

wherein

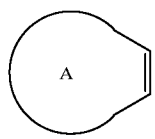

represents:
a) 5- or 6-membered heterocyclyl containing one, two or three double bonds, but at least one double bond and 1, 2 or 3 heteroatoms selected from O, N and S, the heterocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$,
b) 5- or 6-membered carbocyclyl containing one or two double bonds, but at least one double bond, the carbocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2C_8$ alkynyl, or $C_3$–$C_8$ cycloalkyl, $CO(CH_2)_nCH_3$, and $CO(CH_2)_nCH_2N(R^5)_2$,
c) aryl, wherein aryl is as defined below,
    $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, $CO(CH_2)_nCH_3$, and $CO(CH_2)_nCH_2N(R^5)_2$,
    aryl is defined as phenyl or naphthyl, which is unsubstituted or substituted with one, two or three substituents selected from the group consisting of: OH, $CO_2R^4$, Br, Cl, F, I, $CF_3$, $N(R^5)$, $C_1$–$C_8$ alkoxy, $C_1C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$, and when two substituents are located on adjacent carbons they can join to form a 5- or 6-membered ring with one, two or three heteroatoms selected from O, N, and S, which is unsubstituted or substituted with one, two or three substituents selected from the group consisting of: H, OH, $CO_2R^6$, Br, Cl, F, I, $CF_3$, $N(R^7)_2$, $C_1$–$C_8$ alkoxy, $C_1$–$C_8$ alkyl, $C_2$–$C_8$ alkenyl, $C_2$–$C_8$ alkynyl, or $C_3C_8$ cycloalkyl, $CO(CH_2)_nCH_3$, and $CO(CH_2)_nCH_2N(R^5)_2$,
    n is 0 to 5;

$R^1$ is:
a) $C_1$–$C_8$ alkyl, $C_2$–$C_8$ alkenyl, $C_2$–$C_8$ alkynyl, $C_3C_8$ cycloalkyl,
b) aryl, or
c) heteroaryl;
    heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, $R^2$ is $OR^4$ or $N(R^5)_2$;

$R^3$ is

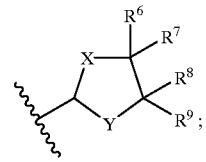

$R^{3a}$ is:
a) CHO,
b) —CO-$C_1$–$C_8$ alkyl,
c) —CO-aryl, or
d) —CO-heteroaryl;

X and Y are independently: O, S, or $NR^5$;

$R^4$ is $C_1$–$C_8$ alkyl;

$R^5$ is: $C_1$–$C_8$ alkyl, or aryl; and $R^6$, $R^7$, $R^8$ and $R^9$ are independently: H, $C_1$–$C_8$ alkyl, and aryl, such that either $R^6$ and $R^7$ are not the same and/or $R^8$ and $R^9$ are not the same, or $R^6$ and $R^8$ or $R^7$ and $R^9$ can join to form a 5- or 6-membered ring, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$;

comprising reacting a α,β-unsaturated ester or amide

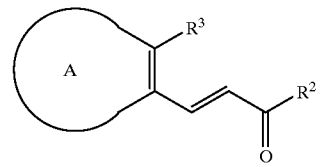

with an organolithium compound, $R^1Li$, in the presence of an aprotic solvent at a temperature range of about −78° C. to about 0° C.

2. The process as recited in claim 1, wherein the number of equivalents of the organolithium compound, $R^1Li$, is 1 to about 4.

3. The process as recited in claim 2, wherein the aprotic solvent is selected from the group consisting of tetrahydrofuran, diethyl ether, methyl t-butyl ether, benzene, toluene, hexane, pentane, dioxane and a mixture of said solvents.

4. The process as recited in claim 3, wherein the temperature range is about −78° C. to about −20° C.

5. A process for the preparation of a compound of formula I:

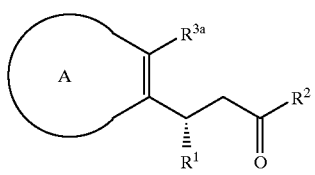

wherein

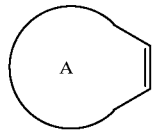

represents:
a) 5- or 6-membered heterocyclyl containing one, two or three double bonds, but at least one double bond and 1, 2 or 3 heteroatoms selected from O, N and S, the heterocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$,
b) 5- or 6-membered carbocyclyl containing one or two double bonds, but at least one double bond, the carbocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$,
c) aryl, wherein aryl is as defined below,
$C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, $CO(CH_2)_nCH_3$, and $CO(CH_2)_nCH_2N(R^5)_2$,
aryl is defined as phenyl or naphthyl, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$, and when two substituents are located on adjacent carbons they can join to form a 5- or 6-membered ring with one, two or three heteroatoms selected from O, N, and S, which is unsubstituted or substituted with one, two or three substituents selected from the group consisting of: H, OH, $CO_2R^6$, Br, Cl, F, I, $CF_3$, $N(R^7)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$,
n is 0 to 5;

$R^1$ is:
a) $C_1$–$C_8$ alkyl, $C_2$–$C_8$ alkenyl, $C_2$–$C_8$ alkynyl, $C_3$–$C_8$ cycloalkyl,
b) aryl, or
c) heteroaryl;

heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$;

$R^2$ is $OR^4$ or $N(R^5)_2$;

$R^3$ is

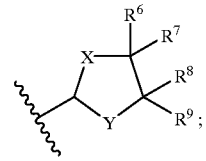

$R^{3a}$ is:
a) CHO,
b) —CO-$C_1$–$C_8$ alkyl,
c) —CO-aryl, or
d) —CO-heteroaryl;

X and Y are independently: O, S, or $NR^5$;

$R^4$ is $C_1$–$C_8$ alkyl;

$R^5$ is: $C_1$–$C_8$ alkyl, or aryl; and $R^6$, $R^7$, $R^8$ and $R^9$ are independently: H, $C_1$–$C_8$ alkyl, and aryl, such that either $R^6$ and $R^7$ are not the same and/or $R^8$ and $R^9$ are not the same, or $R^6$ and $R^8$ or $R^7$ and $R^9$ can join to form a 5- or 6-membered ring, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$;

comprising the steps of:
1) reacting an α,β-unsaturated ester or amide

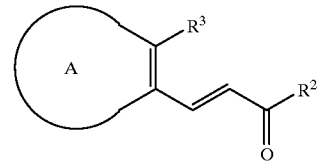

with an organolithium compound, $R^1Li$, in the presence of an aprotic solvent at a temperature range of about −78° C. to about 0° C. to give the conjugate adduct; and
2) removing the chiral auxiliary, $R^3$, with aqueous acid and tetrahydrofuran to give the compound of Formula I.

6. The process as recited in claim 5, wherein the number of equivalents of the organolithium compound, $R^1Li$, is 1 to about 4.

7. The process as recited in claim 6, wherein the aprotic solvent is selected from the group consisting of tetrahydrofuran, diethyl ether, methyl t-butyl ether, benzene, toluene, hexane, pentane, dioxane and a mixture of said solvents.

8. The process as recited in claim 7, wherein the temperature range is about −78° C. to about −20° C.

9. The process as recited in claim 8, wherein the aqueous acid is aqueous acetic acid.

10. A process for the preparation of

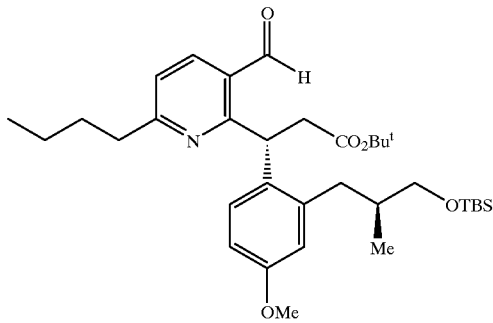

comprising reacting a α,β-unsaturated ester or amide

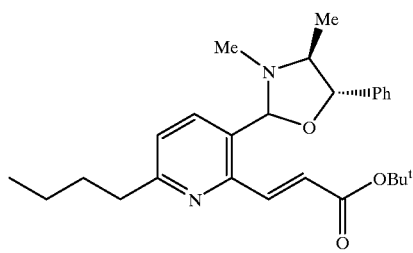

with an organolithium compound

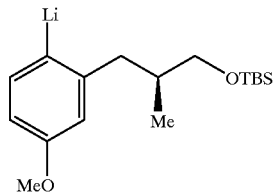

in the presence of an aprotic solvent at a temperature range of about −78° C. to about −20° C.

11. The process as recited in claim 10, wherein the number of equivalents of the organolithium compound, $R^1Li$, is 1 to about 4.

12. The process as recited in claim 11, wherein the aprotic solvent is selected from the group consisting of tetrahydrofuran, diethyl ether, methyl t-butyl ether, benzene, toluene, pentane, hexane, dioxane and a mixture of said solvents.

13. The process as recited in claim 12, wherein the temperature range is about −78° C. to about −50° C.

14. The process as recited in claim 13, wherein the number of equivalents of the organolithium compound, $R^1Li$, is 1.5 to about 2.5.

15. The process as recited in claim 14, wherein the aprotic solvent is tetrahydrofuran.

16. The process as recited in claim 15, wherein the temperature range is about −78° C. to about −70° C.

17. A process for the preparation of a ketone

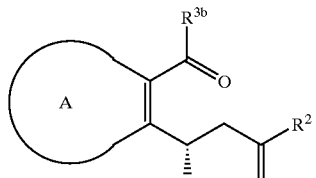

wherein

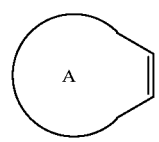

represents:
a) 5- or 6-membered heterocyclyl containing one, two or three double bonds, but at least one double bond and 1, 2 or 3 heteroatoms selected from O, N and S, the heterocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$,
b) 5- or 6-membered carbocyclyl containing one or two double bonds, but at least one double bond, the carbocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$,
c) aryl, wherein aryl is as defined below,
  $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, $CO(CH_2)_nCH_3$, and $CO(CH_2)_nCH_2N(R^5)_2$,
  aryl is defined as phenyl or naphthyl, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$, and when two substituents are located on adjacent carbons they can join to form a 5- or 6-membered ring with one, two or three heteroatoms selected from O, N, and S, which is unsubstituted or substituted with one, two or three substituents selected from the group consisting of: H, OH, $CO_2R^6$, Br, Cl, F, I, $CF_3$, $N(R^7)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$,
  n is 0 to 5;
$R^1$ is:
a) $C_1$–$C_8$ alkyl, $C_2$–$C_8$ alkenyl, $C_2$–$C_8$ alkynyl, $C_3$–$C_8$ cycloalkyl,
b) aryl, or
c) heteroaryl;
  heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $N(R^5)_2$, $C_1-C_8$ alkoxy, $C_1-C_8$ alkyl, $C_2-C_8$ alkenyl, $C_2-C_8$ alkynyl, or $C_3-C_8$ cycloalkyl, $CO(CH_2)_nCH_3$, and $CO(CH_2)_nCH_2N(R^5)_2$, $R^2$ is $OR^4$ or $N(R^5)_2$;

$R^3$ is 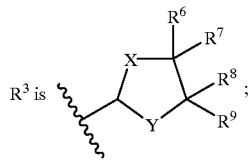;

$R^{3b}$ is:
a) $C_1-C_8$ alkyl,
b) aryl, or
c) heteroaryl;

X and Y are independently: O, S, or $NR^5$;

$R^4$ is $C_1-C_8$ alkyl;

$R^5$ is: $C_1-C_8$ alkyl, or aryl; and $R^6$, $R^7$, $R^8$ and $R^9$ are independently: H, $C_1-C_8$ alkyl, and aryl, such that either $R^6$ and $R^7$ are not the same and/or $R^8$ and $R^9$ are not the same, or $R^6$ and $R^8$ or $R^7$ and $R^9$ can join to form a 5- or 6-membered ring, which is unsubstituted or substituted with one, two or three substituents selected from the group consisting of: OH, $CO_2R^4$, Br, Cl, F, I, $CF_3$, $N(R^5)_2$, $C_1-C_8$ alkoxy, $C_1-C_8$ alkyl, $C_2-C_8$ alkenyl, $C_2-C_8$ alkynyl, or $C_3-C_8$ cycloalkyl, $CO(CH_2)_nCH_3$, $CO(CH_2)_nCH_2N(R^5)_2$;

comprising the steps of:

reacting a α,β-unsaturated ester or amide

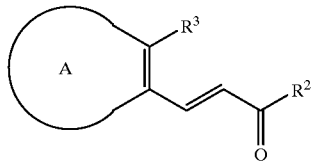

with an organolithium compound, $R^1Li$, in the presence of an aprotic solvent at a temperature range of about −78° C. to about 0° C. to give a conjugate adduct

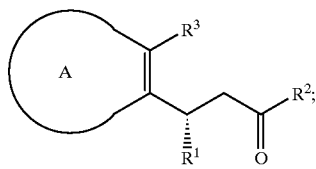

2) removing the chiral auxiliary with aqueous acid and tetrahydrofuran to give the aldehyde

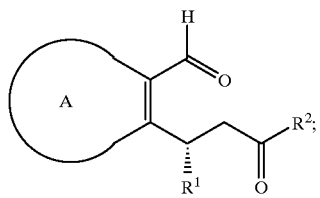

3) reacting the aldehyde with a Grignard reagent or organolithium reagent formed with $R^{3b}Z$, where Z is Br, Cl, or I to form an alcohol

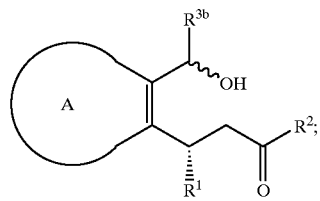

4) oxidizing the alcohol formed with an oxidizing agent to give the ketone

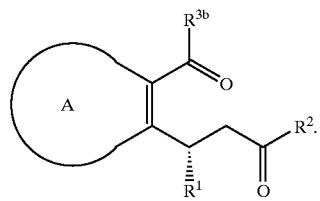

18. The process as recited in claim 17, wherein the number of equivalents of the organolithium compound in the first step is 1 to about 4.

19. The process as recited in claim 18, wherein the aprotic solvent in the first step is selected from the group consisting of tetrahydrofuran, diethyl ether, methyl t-butyl ether, benzene, toluene, pentane, hexane, dioxane and a mixture of said solvents.

20. The process as recited in claim 19, wherein the temperature range in the first step is about −78° C. to about −50° C.

21. The process as recited in claim 20, wherein the aqueous acid in the second step is aqueous acetic acid.

22. The process as recited in claim 21, wherein the oxidizing agent in the forth step is 4-methylmorpholine-N-oxide and tetrapropylammonium perruthenate(VII).

23. A process for the preparation of a ketone of formula:

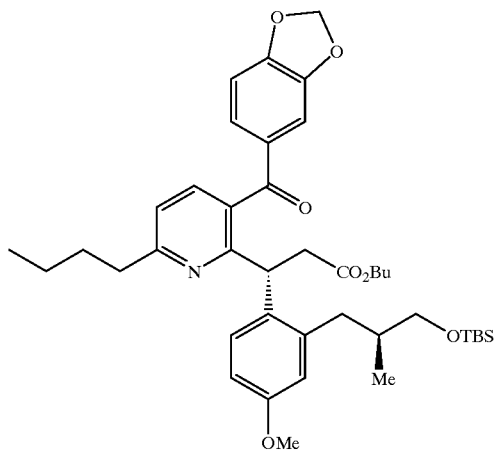

comprising the steps of:
1) reacting a α,β-unsaturated ester or amide

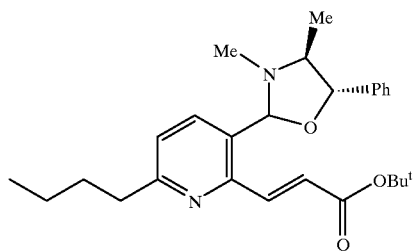

with an organolithium compound

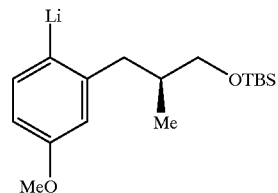

in the presence of an aprotic solvent at a temperature range of about −78° C. to about −20° C. to give a conjugate adduct

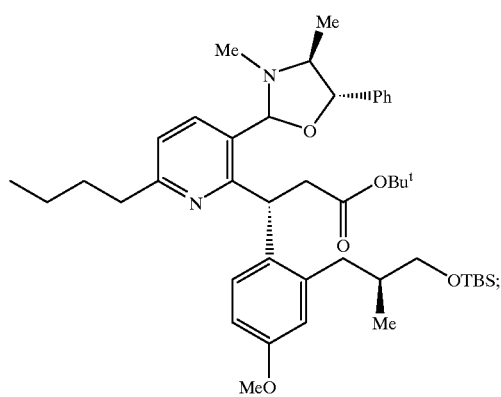

2) removing the chiral auxiliary with aqueous acid and tetrahydrofuran to give the aldehyde

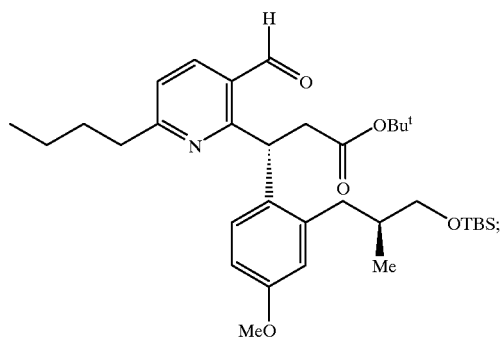

3) reacting the aldehyde with a Grignard reagent or organolithium reagent formed with

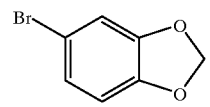

to form the alcohol

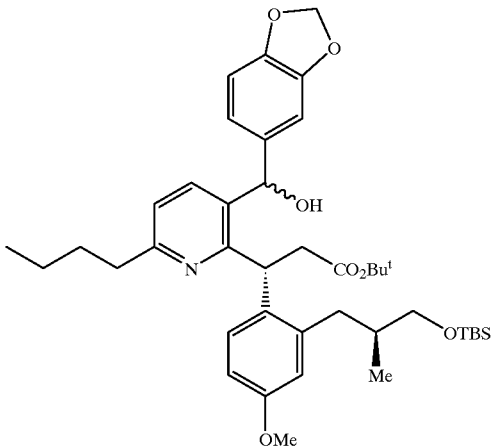

4) oxidizing the alcohol formed with an oxidizing agent to give a ketone

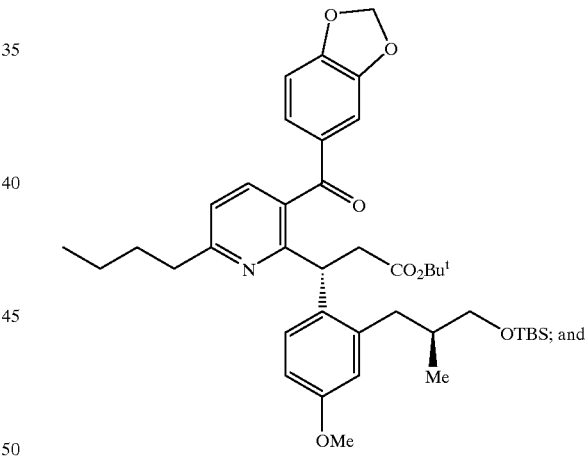

5) transesterifying the ester with n-butanol and a Lewis acid to give the desired ketone.

24. The process as recited in claim 23, wherein the number of equivalents of the organolithium compound in the first step is 1 to about 4.

25. The process as recited in claim 24, wherein the aprotic solvent in the first step is selected from the group consisting of tetrahydrofuran, diethyl ether, methyl t-butyl ether, benzene, toluene, pentane, hexane, dioxane and a mixture of said solvents.

26. The process as recited in claim 25, wherein the temperature range in the first step is about −78° C. to about −50° C.

27. The process as recited in claim 26, wherein the aqueous acid in the second step is aqueous acetic acid.

28. The process as recited in claim 27, wherein the Grignard reagent in the third step is

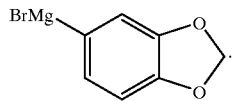

29. The process as recited in claim 27, wherein the organolithium reagent in the third step is

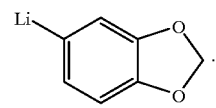

30. The process as recited in claim 28, wherein the oxidizing agent in the forth step is 4-methylmorpholine-N-oxide and tetrapropylammonium perruthenate(VII).

31. The process as recited in claim 30, wherein the fifth step is conducted in the presence of a Lewis acid selected from the group consisting of: $Ti(OEt)_4$, $Ti(OiPr)_4$, and $Ti(OBu)_4$.

* * * * *